(12) United States Patent
De La Torre et al.

(10) Patent No.: US 12,109,041 B2
(45) Date of Patent: Oct. 8, 2024

(54) BIOMETRIC AWARENESS TRAINING PLATFORM AND METHOD OF MONITORING PHYSIOLOGICAL RESPONSES

(71) Applicants: Gonzalo De La Torre, Eagle, ID (US); Marianna Budnikova, Seattle, WA (US); Daniel Thurber, Meridian, ID (US)

(72) Inventors: Gonzalo De La Torre, Eagle, ID (US); Marianna Budnikova, Seattle, WA (US); Daniel Thurber, Meridian, ID (US)

(*) Notice: Subject to any disclaimer, the term of this patent is extended or adjusted under 35 U.S.C. 154(b) by 619 days.

(21) Appl. No.: 17/462,959

(22) Filed: Aug. 31, 2021

(65) Prior Publication Data

US 2022/0061757 A1 Mar. 3, 2022

Related U.S. Application Data

(60) Provisional application No. 63/073,639, filed on Sep. 2, 2020.

(51) Int. Cl.
| | |
|---|---|
| *A61B 5/02* | (2006.01) |
| *A61B 5/00* | (2006.01) |
| *A61B 5/021* | (2006.01) |
| *A61B 5/024* | (2006.01) |
| *A61B 5/08* | (2006.01) |
| *A61B 5/145* | (2006.01) |
| *G02B 27/01* | (2006.01) |
| *G06F 3/01* | (2006.01) |

(52) U.S. Cl.
CPC .......... *A61B 5/4884* (2013.01); *A61B 5/021* (2013.01); *A61B 5/024* (2013.01); *A61B 5/0816* (2013.01); *A61B 5/14532* (2013.01); *A61B 5/6801* (2013.01); *G02B 27/017* (2013.01); *G06F 3/011* (2013.01)

(58) Field of Classification Search
CPC ....... G06F 3/011; A61B 5/4884; A61B 5/021; A61B 5/024; A61B 5/14532
See application file for complete search history.

(56) References Cited

U.S. PATENT DOCUMENTS

| | | | | |
|---|---|---|---|---|
| 10,242,501 | B1* | 3/2019 | Pusch | H04N 21/44218 |
| 10,448,866 | B1* | 10/2019 | German | G10L 15/22 |
| 11,191,466 | B1* | 12/2021 | Heneghan | A61B 5/01 |
| 2014/0236953 | A1* | 8/2014 | Rapaport | G06F 16/285 |
| | | | | 707/740 |
| 2016/0008632 | A1* | 1/2016 | Wetmore | A61N 1/36025 |
| | | | | 607/45 |

(Continued)

*Primary Examiner* — Eliyah S. Harper
(74) *Attorney, Agent, or Firm* — Whitley Legal Group, PC; AnnMarie W Whitley

(57) ABSTRACT

A biometric awareness training platform and method of monitoring, evaluating, and training a participant's physiological response to stimulation employs a content delivery system for providing variable content to the participant, a physiological tracking system to measure physiological responses as the participant experiences the delivered content, and a progress tool for delivering an actionable status based on the participant's measured physiological responses. The progress tool evaluates the physiological response measurements to provide a status indicator such as green, yellow, or red representing the participant's current physiological status.

20 Claims, 3 Drawing Sheets

(56) References Cited

U.S. PATENT DOCUMENTS

| | | | |
|---|---|---|---|
| 2017/0324437 A1* | 11/2017 | Ruttler | G08B 21/0211 |
| 2018/0161626 A1* | 6/2018 | Fung | G16H 40/63 |
| 2020/0219615 A1* | 7/2020 | Rabin | G16H 50/30 |
| 2020/0225655 A1* | 7/2020 | Cella | G05B 19/41875 |
| 2020/0253527 A1* | 8/2020 | Ellison | A61B 5/165 |
| 2021/0030308 A1* | 2/2021 | Grace | A61B 5/486 |
| 2021/0074417 A1* | 3/2021 | Pierson | G06F 8/65 |
| 2022/0359064 A1* | 11/2022 | Pierson | G08B 25/005 |

* cited by examiner

BIOMETRIC AWARENESS TRAINING PLATFORM AND METHOD OF MONITORING PHYSIOLOGICAL RESPONSES

CROSS-REFERENCE TO RELATED APPLICATIONS

This application claims the benefit of provisional U.S. Application 63/073,639 filed Sep. 2, 2020.

FIELD OF INVENTION

This invention relates to a system and method for monitoring, evaluating, and training a user's physiological responses to real-time and simulated stimulation. More particularly, this invention relates to a content delivery apparatus and physiological tracking system that can be used to evaluate, select, and train individuals regularly exposed to dynamic environments or diverse populations.

BACKGROUND

First responders, public servants, customer service representatives, teachers, cashiers, and many others regularly interact with a diverse population, find themselves operating in a dynamic environment, or both. The ability to adapt when the situation rapidly changes or to respond without bias can be challenging for many people. Unfortunately, when one's decision-making ability is compromised because of sensory overload or due to considerations of irrelevant factors such as age, ethnicity, weight, gender, or even hair color, one is more likely to make mistakes, and poor outcomes are more likely. Accordingly, there is a great need for systems that identify individuals who might falter in high pressure environments and those who might react to situations or others differently due to unconscious bias. Moreover, a system is also needed for training those individuals to improve their resilience and to eliminate the impact of their implicit bias.

To train individuals to become resilient and adaptive in a dynamic environment, educators and employers often focus on improving self-talk, developing a positive outlook, being prepared, recognizing mistakes, and building on past successes. Additionally, for some professions where stress and adversity are regularly experienced and encountered, specialized training aims to increase skills and improve outcomes through repeated exposure. For example, firefighters might regularly complete training on firearms, hazmat, defensive tactics, dealing with emotionally or mentally ill citizens, crisis management, driving skills, verbal skills, first aid, CPR, and medical training.

As with improving resilience, to combat implicit or unconscious bias, educators and employers often focus on recognition and mindfulness. Through educational programming, in particular, participants are taught to recognize what biases they may hold, how their biases connect to being a person of power, and how their biases and power influence or inform their interactions with people. Additionally, participants also learn how to build empathy, practice mindfulness, and appreciate group differences and multicultural viewpoints. By raising awareness, employers can minimize the impact of bias when hiring and evaluating others, provide greater access to mentorship opportunities for all of its employees, operate with greater transparency, and provide a better service or product for their customers.

While educational and job-specific training exists both for improving resiliency and mitigating bias, a tool or platform is needed for testing one's progress using objective markers and for providing actionable feedback on a regular basis. Unfortunately, a well-intentioned professional might not consider some sources of stress or bias, which can cause them to miss areas of improvement, and even the best-trained professional can have a bad day, which can impact their performance on the job on that day.

Accordingly, it would be desirable to provide a system and method for providing simulated situations involving dynamic environments and different populations in order to evaluate one's resilience and bias and to measure improvement. It would be further desirable to provide a system that records one's physiological response when exposed to dynamic environments and diverse populations in order to accurately assess challenges using objective data points and to train one to recognize or become aware of his or her physiological responses when stressed. It also would further be desirable to provide a system and method for assessing one's resilience or the impact of one's unconscious bias on a regular basis to identify out of the ordinary patterns of response or behavior.

SUMMARY OF THE INVENTION

A biometric awareness training platform and method of monitoring, evaluating, and training a participant's physiological response to stimulation employs a content delivery system for providing variable content to the participant, a physiological tracking system to measure physiological responses as the participant experiences the delivered content, and a progress tool for delivering an actionable status based on the participant's measured physiological responses. The content delivery system uses traditional two-dimensional displays or virtual reality (VR), augmented reality (AR), or mixed reality (MR) delivery methods and equipment such as a head mounted display (HMD) with a computer to provide reenacted or simulated target content, both filmed and volumetric. The physiological tracking system includes one or more sensors for measuring the physiological response of the participant while viewing the target content. Such sensors measure, for example, heart rate, heart rate variability, electrical brain activity through an electroencephalogram (EEG), heart activity through an electrocardiogrameurofeedback, biofeedback, saccadic eye movements, saccadic eye masking, respiration rate, blood pressure, pupil size, perspiration, blood glucose, average sleep/wake hours, and daily REM average. The progress tool is stored and executable by a computer system, and it evaluates the biometric response measurements to provide a status indicator such as green, yellow, or red. The progress tool compares the participant's recorded physiological response measurements to one or more databases or constants, assesses the level of stress, bias, aggression, and/or other physiological engagement, and provides a code, symbol, or other indicator that represents the participant's current physiological status. The status indicator can be used for a wide variety of purposes including the participant, an employer, or any other interested party to track progress, to train for diverse or dynamic conditions, to determine daily job assignments, to assess safety conditions, when making employment offers, or when engaging in self-improvement. Additionally, a participant can use feedback from the progress tool to increase self-awareness and recognize physiological changes even when not using the physiological tracking system or training platform. Ideally, through regular use of the biometric awareness platform, a participant can learn to independently recognize warning signs and self-assess his or her physiological status.

For a better understanding of the invention reference is made to the following detailed description of the preferred embodiments of the invention which should be taken in conjunction with the above described drawings.

DETAILED DESCRIPTION OF THE INVENTION

Figure 1:
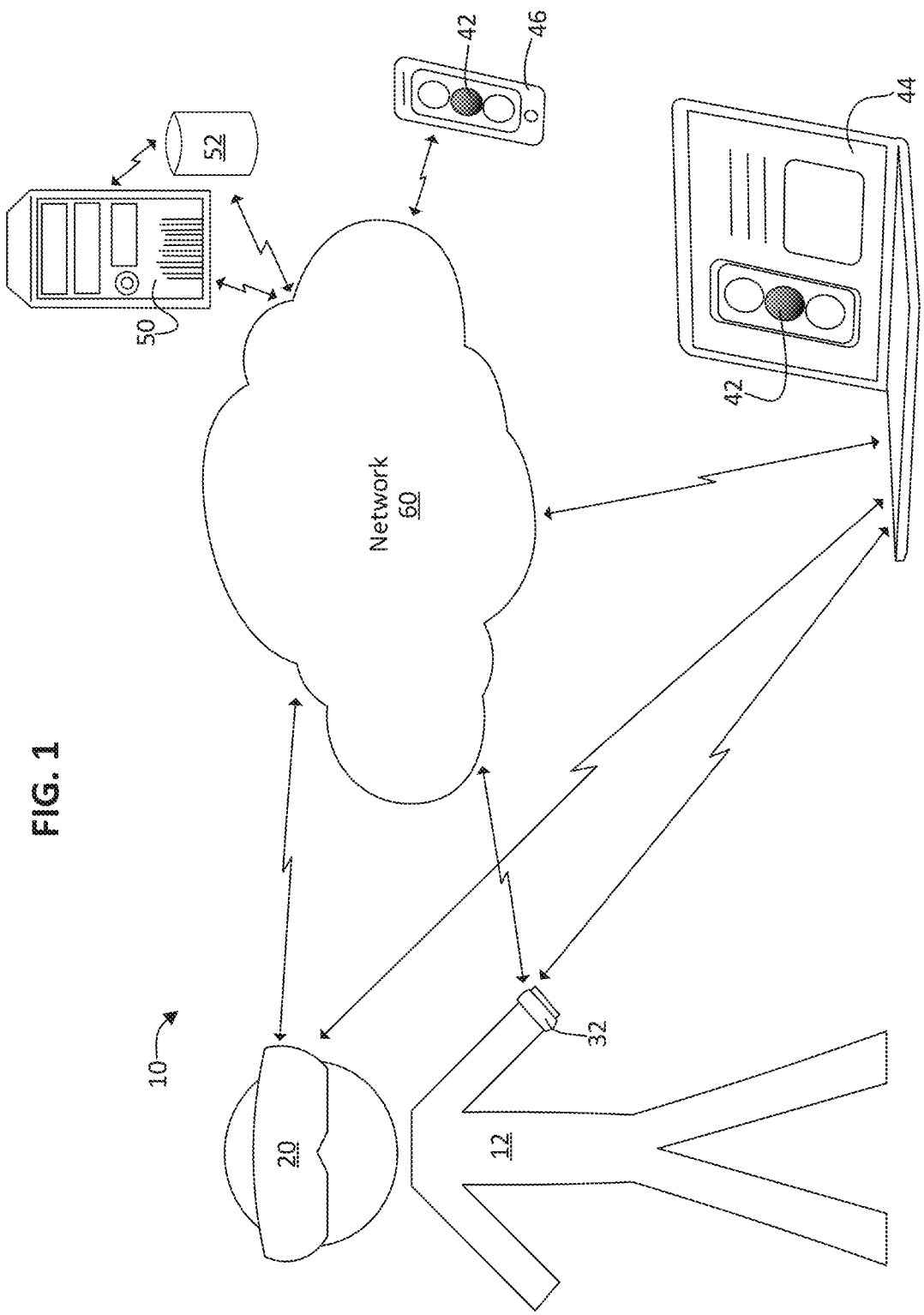
FIG. 1 is a diagram of the connected components of the present invention.
Figure 2:
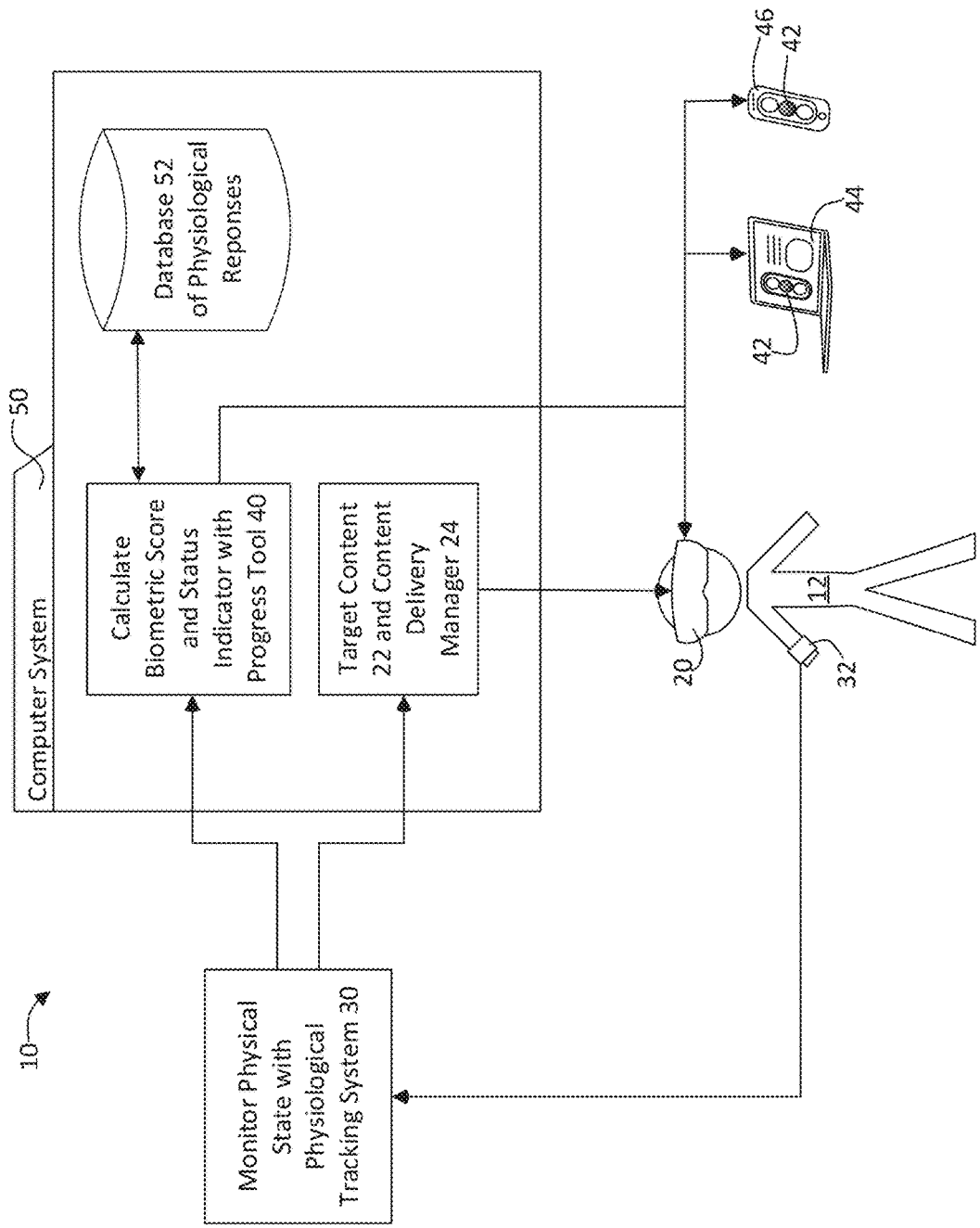
FIG. 2 is a diagram of the method of evaluating a participant's biometric awareness according to the present invention.

A biometric awareness training platform 10 and method of monitoring, evaluating, and training the physiological responses of a participant 12 to stimulation is shown in FIGS. 1 and 2. Platform 10 includes a content delivery system 20 for providing variable content to the participant, a physiological tracking system 30 to measure biometric responses as the participant experiences the delivered content, and a progress tool 40 stored on and executable by a computer system 50 for delivering an actionable status 42 to one or more displays 20, 42, 46 based on the participant's measured physiological responses.

The content delivery system 20 uses traditional two-dimensional displays or virtual reality (VR), augmented reality (AR), or mixed reality (MR) delivery methods and equipment such as a brain implant or head mounted display (HMD) with a computer to provide reenacted or simulated target content, both filmed and volumetric. As shown in FIGS. 1 and 2, content delivery system 20 is an HMD. Alternatively, the delivery system 20 can be any display capable of delivering audio and video content including mobile devices and personal computers. Preferably, system 20 includes communication means for receiving instructions from other devices and for communicating through a local or cloud-based network 60. Additionally, content delivery system 20 preferably includes computing components such as storage and a processor capable of storing and executing software, which may include all or some components of a content delivery manager 24 program capable of adjusting aspects of the delivered target content 22 in increments as needed or as directed and optionally according to instructions received from other devices of platform 10, such as where the target content 22 might increase in intensity to challenge the participant's physiological response, desensitize the participant 12, or otherwise train the participant's threshold for quality outcome.

The content delivery system 20 delivers selected target content 22 to the participant and optionally information from other components of platform 10 such as the status 42 generated by progress tool 40. The target content 22 preferably is reenacted or simulated content, filmed or volumetric. For HMDs and implants/laser retinal reflections, the content is preferably mixed, augmented, or virtual reality three dimensional and 360 degree video and volumetric content. For standard two dimensional screens, the content is preferably traditional film. The target content 22 may be non-interactive or interactive, and preferably various features of the content can be varied or selected. For example, target content 22 might include actors of different sexes, genders, ages, ethnicities, or aggressiveness and might vary as to levels of exposure or risk (e.g., fire intensity levels, environmental conditions, crowds, hostility, etc.).

The physiological tracking system 30 includes one or more sensors 32 for measuring the physiological response of the participant 12 while viewing the target content 22. Such sensors 32 measure, for example, heart rate, heart rate variability, respiration rate, oxygen saturation, blood pressure, pupil size, perspiration, blood glucose, electrical brain activity through an EEG, heart activity through an EKG, neurofeedback, biofeedback, saccadic eye movements, saccadic eye masking, average sleep/wake hours, and daily REM average. Data collected form the sensors 32 includes one or more sets of physiological data that can be delivered through wired or wireless communication to other components of platform 10. Preferably the collected physiological data is delivered via wireless connection to the content delivery system 20 for optional processing by the content delivery manager and to the computer system 50 storing and executing the progress tool 40 for evaluation and eventual calculation of a physiological status.

Preferably, tracking system 30 includes several sensors 32 for use simultaneously or selectively. Alternatively, tracking system 30 includes one or only a few sensors 32 especially if portability is desired. For example, if a participant 12 is a first responder who uses platform 10 while in the field, tracking system 30 might include only a portable blood pressure monitor or a pulse oximeter that the first responder wears while watching target content 22 on his or her mobile phone or an HMD. If participant 12 is an educator, however, tracking system 30 might include multiple sensors all of which the educator applies and wears while watching target content 22 on a series of displays or screens in a dedicated training room at participant's educational institution.

Platform 10 includes a computer system 50 having control and processing components such as a processor, memory, input and output components, and wireless or wired communication components as is well known in the art. Computer system 50 can be a computing environment with one or more computing devices including an independent component within platform 10, a combination of components across platform 10, or integral with any individual component of platform 10. Preferably, computer system 50 connects with other components wirelessly over a network 60. Wireless communications components include near field communication components, the wireless communications components discussed above, and longer range communications components to facilitate communication with the various platform 10 elements and to facilitate communication with software and content located remotely or accessible only via the Internet. Software can be stored on the computer system's memory and is preferably executable by the processor to perform many tasks. For example, the progress tool software can be stored in computer system 50 and used to calculate a physiological status indicator based on standard physiological data ranges or constants retrieved from a database 52 (locally stored or accessed over a network) and collected physiological data of the participant 12.

The progress tool 40 evaluates the recorded physiological response measurements of a participant 12 during a training session. The tool 40 also determines and communicate to a status delivery system a status indicator 42, such as green, yellow, or red. The progress tool uses computer system 50 to store and execute software that compares the collected physiological data to one or more databases containing reference or standard physiological data ranges or constants, assesses the level of stress, bias, aggression, and/or other physiological engagement, and provides a code, symbol, or other indicator 42 that represents the participant's current physiological status. The progress tool can be set to produce a simple three-part status such as Red, Yellow, or Green, or it can produce status results using other comparative means such as a rating of 1 through 10 or a dial from 0 to 60. Additionally, the progress tool 40 can be adapted to store and track physiological data or status over time or to aggregate and/or average status over time.

Once a training session is complete, or optionally in real-time, the participant 12 and others can view the participant's status on the status delivery system such as one or more displays or devices 44, 46, including optionally on a display of the content delivery system 20. Displays or devices can be any type of display capable of displaying status indicators including, for example, mobile devices, personal computers, watches, automobile displays, televisions, HMDs. Displays can also include other forms of visually representing information such as LED lights. Additionally, display can include non-visual methods of delivering information including through audible and tactile means.

The progress tool 40 preferably receives the following recorded data from the physiological tracking system 30 sensors: heart rate, respiration rate, blood pressure, pupil size, perspiration rate, and blood sugar levels. Using that data, a biometric score is calculated. Preferably, a biometric score is calculated according to the following formula:

Biometric Score(Score) =(heart rate)*α+(respiration rate)*β+(blood pressure)*ə+(pupil size)*Ω+ (persperation rate)*μ+(blood sugar level)*v where α, β, ə, Ω, μ, and v are all coefficients of importance of each of the participant's response measurement. Alternatively, the biometric score can be calculated using additional variables and constants or with another equation that takes into consideration the collected data. After calculating the biometric score, the score is run through a threshold function, f(Score, γ, θ), to calculate the biometric status for the current participant state. Specifically, where Score <θ, then the calculated Score falls within a first range corresponding to a first status, e.g., Green. Where θ<Score <γ, then the calculated Score falls within a second range corresponding to a second status, e.g., Yellow. Where Score >γ, then the calculated Score falls within a third range corresponding to a third status, e.g., Red.

Preferably, the physiological data collected from the participant during a training session occurs at regular intervals (e.g., every second) and a Score and status is calculated at each interval. More preferably, the Scores collected at each interval are averaged to provide the participant with an overall status indicator for his or her training session:

$$\text{Average Score} = \frac{\sum(\text{Scores } 1 - n)}{n}$$

Optionally, a participant might receive several status indicators 42 related to several individual Scores and a status indicator 42 relating to his or her average or overall Score.

Figure 3:
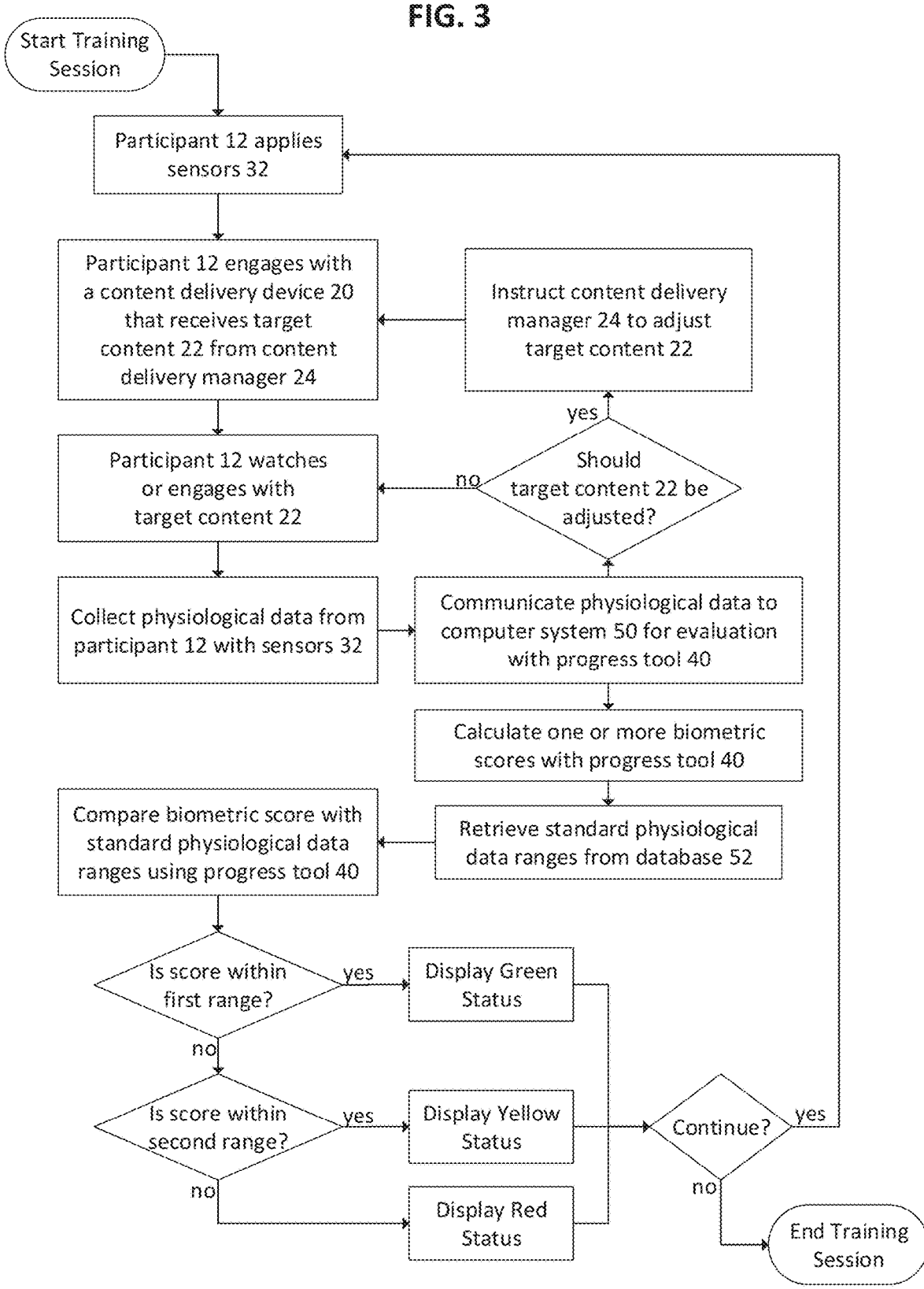
FIG. 3 is a flowchart illustrating the steps to evaluate a participant's physiological status according to the present invention.

FIG. 3 illustrates a method of use of platform 10 by a participant 12 during a biometric awareness training session, which includes evaluations and other uses of platform 10 in addition to training sessions. First, a participant applies the sensors 32 where appropriate. For example, the participant places a blood pressure monitor on his or her arm. The participant next engages with the content viewing device 20 on which target content 22 is displayed according to instructions received from the content delivery manager 24. For example, the participant puts on an HMD that wirelessly receives content 22 managed by software a nearby computer system 50. The participant then watches the target content 22 and, where appropriate, engages with the content while the sensors 32 record physiological data and communicate them to a local or remote computer system 50 over an optional network 60. Optionally, the physiological data can first be considered by a content management program stored on the computer system 50 to determine if adjustments to the target content 22 are desirable. If they are, the content delivery manager 24 can be instructed to do so. At the same time, using the progress tool 40 that is also stored on the computer system 50, one or more biometric scores are calculated. An average of the scores, individual scores, or some combination can be compared to standard physiological data ranges or constants to determine what range the participant's biometric score falls within. After determining the range where the participant's biometric score falls, a status indicator 42 (e.g., symbol, color, number, dial, etc.) can be displayed on one or more devices or displays 20, 44, 46. For example, if the participant's biometric score is low, he or she may see an image of a stoplight on his or her mobile device 46 with the color green illuminated.

The status indicator 42 can be used by the participant 12, an employer, or any other interested party for a wide variety of reasons including to track progress, to train for diverse or dynamic conditions, to determine daily job assignments, to assess safety conditions, when making employment offers, or when engaging in self-improvement. The status indicator 42 also can be transmitted to behavioral health specialists or supervisors to ameliorate situations that are triggered by certain environments or populations. Additionally, a participant 12 can use feedback from the progress tool to increase self-awareness and recognize physiological changes even when not using the physiological tracking system 30 or platform 10. Ideally, through regular use of the biometric awareness platform 10, a participant can learn to independently recognize warning signs and self-asses his or her physiological status.

While there has been illustrated and described what is at present considered to be the preferred embodiment of the present invention, it will be understood by those skilled in the art that various changes and modifications may be made and equivalents may be substituted for elements thereof without departing from the true scope of the invention disclosed, but that the invention will include all embodiments falling within the scope of the claims.

We claim:

1. A biometric awareness training platform comprising:
    a) a content delivery system positioned to deliver content to a participant;
    b) a status delivery system positioned to deliver content to a participant;
    c) a physiological tracking system comprising at least two sensors disposed on or near the participant to measure the physiological response of the participant; and
    d) a progress tool in communication with the physiological tracking system and the status delivery system comprising:
        i) a memory device;
        ii) a processing device configured to cause the tool to:

a) access the physiological response measured by the physiological tracking system sensors and generate a sensor measurement corresponding to each sensor disposed on or near the participant;
b) simplify the physiological response into a participant biometric score by:
   i) multiplying each sensor measurement by a corresponding coefficient stored on the memory device to generate a modified sensor measurement corresponding to each sensor; and
   ii) adding together the modified sensor measurements;
c) compare the participant biometric score to reference biometric scores stored on the memory device;
d) generate a status indicator based on the comparison of the participant biometric score to the reference biometric scores; and
e) communicate the status indicator to the status delivery system.

2. The biometric awareness training platform of claim 1 wherein the content delivery system comprises a head mounted display.

3. The biometric awareness training platform of claim 1 wherein the content delivery system is configured to deliver virtual reality content, augmented reality content, or mixed reality content.

4. The biometric awareness training platform of claim 1 wherein the content delivery system comprises a content delivery manager tool comprising a memory device and a processing device configured to cause the tool to receive instructions from an input device and adjust the content delivered to the participant according to the instructions received.

5. The biometric awareness training platform of claim 1 wherein:
a) the physiological tracking system comprises a first sensor for measuring a participant's heart rate, a second sensor for measuring a participant's respiration rate, a third sensor for measuring a participant's blood pressure, a fourth sensor for measuring a participant's pupil size, a fifth sensor for measuring a participant's perspiration rate, and a sixth sensor for measuring a participant's blood sugar level; and
b) the processing device of the progress tool is further programmed to cause the progress tool to simplify the participant's physiological response by:
   i) Generating first, second, third, fourth, fifth, and sixth sensor measurements;
   ii) Modifying the first, second, third, fourth, fifth, and sixth sensor measurements by multiplying each measurement with a corresponding coefficient stored on the memory device; and
   iii) adding together the first, second, third, fourth, fifth, and sixth modified sensor measurements.

6. The biometric awareness training platform of claim 1 wherein the processing device of the progress tool is further programmed to generate an average participant biometric score by recording sensor measurements at regular intervals, generating a biometric score corresponding for each sensor measurement over time, and then averaging the series of generated biometric scores.

7. The biometric awareness training platform of claim 1 wherein the status delivery system is a display, a speaker, or both.

8. The biometric awareness training platform of claim 1 wherein the content delivered to the participant is interactive.

9. A method of monitoring and training a participant's physiological responses to displayed content comprising:
a) applying a first and second sensors to the participant to record the participant's physiological response, wherein each sensor measures a different physiological response of the participant;
b) delivering a first content to the participant;
c) measuring the participant's physiological response to the first content with the first and second sensors;
d) communicating measurements from the first and second sensors to one or more computing devices in a computing environment;
e) executing with the computing devices in the computing environment a computer-implemented method of generating a first participant biometric score associated with the first content, wherein the computer-implemented method of generating a first participant biometric score comprises:
   i) accessing, using the computing devices of the computing environment, first and second stored coefficients;
   ii) multiplying, using the computing devices of the computing environment, the first sensor measurement by a first coefficient to generate a modified first sensor measurement and the second sensor measurement by a second coefficient to generate a modified second sensor measurement; and
   iii) adding, using the computing devices of the computing environment, the first modified sensor measurement to the second modified sensor measurement;
f) executing with the computing devices in the computing environment a computer-implemented method of generating a first status indicator associated with the first content; and
g) communicating from the computing devices in the computing environment to the participant the first status indicator.

10. The method of claim 9 wherein the content delivered to the participant is virtual reality, augmented reality, or mixed reality content.

11. The method of claim 9 wherein the status indicator delivered to the participant is visual, audible, or both.

12. The method of claim 9 further comprising:
a) delivering a second content to the participant;
b) measuring the participant's physiological response to the second content with the first sensor;
c) communicating measurements from the first sensor to the computing devices in the computing environment;
d) using the computing devices in the computing environment, executing a computer-implemented method of generating a second participant biometric score associated with the second content;
e) using the computing devices in the computing environment, executing a computer-implemented method of generating a second status indicator associated with the second content; and
f) communicating from the computing devices in the computing environment to the participant the second status indicator.

13. The method of claim 9 wherein the computer-implemented method of generating the first status indicator comprises comparing, using the computing devices of the computing environment, the participant biometric score with reference biometric scores to determine an appropriate status indicator.

14. The method of claim 13 wherein the computer-implemented method of generating the first biometric score further comprises averaging, using the computing devices of the computing environment, the participant's biometric score taken at regular intervals.

15. A biometric awareness training platform comprising:
   a) a content delivery system positioned to deliver content to a participant;
   b) a status delivery system positioned to deliver content to a participant;
   c) a physiological tracking system disposed on or near the participant to measure the physiological response of the participant, wherein the physiological tracking system comprises a first sensor for measuring a participant's heart rate, a second sensor for measuring a participant's respiration rate, a third sensor for measuring a participant's blood pressure, a fourth sensor for measuring a participant's pupil size, a fifth sensor for measuring a participant's perspiration rate, and a sixth sensor for measuring a participant's blood sugar level; and
   d) a progress tool in communication with the physiological tracking system and the status delivery system comprising:
      i) a memory device;
      ii) a processing device configured to cause the tool to:
         a) access the physiological responses measured by the first, second, third, fourth, fifth, and sixth sensors of the physiological tracking system;
         b) simplify the physiological responses into a participant biometric score;
         c) compare the participant biometric score to reference biometric scores stored on the memory device;
         d) generate a status indicator based on the comparison of the participant biometric score to the reference biometric scores; and
         e) communicate the status indicator to the status delivery system.

16. The biometric awareness training platform of claim 15 wherein the content delivery system is configured to deliver virtual reality content, augmented reality content, or mixed reality content.

17. The biometric awareness training platform of claim 15 wherein the content delivery system comprises a content delivery manager tool comprising a memory device and a processing device configured to cause the tool to receive instructions from an input device and adjust the content delivered to the participant according to the instructions received.

18. The biometric awareness training platform of claim 15 wherein the processing device of the progress tool is further programmed to generate an average participant biometric score by recording sensor measurements at regular intervals, generating a biometric score corresponding for each sensor measurement over time, and then averaging the series of generated biometric scores.

19. The biometric awareness training platform of claim 15 wherein the status delivery system is a display, a speaker, or both.

20. The biometric awareness training platform of claim 15 wherein the content delivered to the participant is interactive.

* * * * *